United States Patent [19]

Bennett

[11] 4,349,083

[45] Sep. 14, 1982

[54] ACOUSTIC EAR MOLD

[76] Inventor: Harry Bennett, 1358 N. Fresno St., Fresno, Calif. 93703

[21] Appl. No.: 253,710

[22] Filed: Apr. 13, 1981

[51] Int. Cl.³ .................................... A61B 7/02
[52] U.S. Cl. .................................... 181/135; 181/130
[58] Field of Search .................... 181/130, 134, 135; 179/1 PC, 107 E, 107 R, 182 R; 128/152

[56] References Cited

U.S. PATENT DOCUMENTS

| | | | |
|---|---|---|---|
| 3,303,902 | 2/1967 | Knott | 181/135 |
| 3,688,863 | 9/1972 | Johnson | 181/135 |
| 4,010,820 | 3/1977 | Johnson | 181/130 X |
| 4,094,315 | 6/1978 | Leight | 128/152 |

*Primary Examiner*—Benjamin R. Fuller
*Attorney, Agent, or Firm*—Huebner & Worrel

[57] ABSTRACT

An acoustic ear mold for intensifying sound pressure for an acoustic signal derived from an electronic hearing aid worn by a patient, characterized by an ear canal component having defined therein a segmented, air-filled resonating cavity including four coaxially aligned, contiguous cavity segments arranged in communicating relation for intensifying sound pressure in the range of 250 hz to 6,000 hz, the diameter of the segments being mutually unique, the lengths of the end-most cavity segments being equal while the axial lengths of the segments interposed between the end-most segments are mutually unique with respect to all other segments of the cavity, a tubular conduit is connected with the cavity for conveying acoustic signals from the hearing aid while an acoustic output chamber extends from the segmented cavity to the terminous of the component for delivering to the tympanic membrane of the wearer, pressure-intensified acoustic signals.

6 Claims, 9 Drawing Figures

ACOUSTIC EAR MOLD

BACKGROUND OF THE INVENTION

The invention generally relates to devices for assisting patients having reduced hearing capabilities and more particularly to an improved ear mold for intensifying the sound produced by a hearing aid, characterized by an electronic amplifier and transducer.

An ear mold, as is readily appreciated by those familiar with such devices, comprising a device made of various types of plastic, both hard and soft, which when inserted into an ear canal and connected to an electronic hearing aid, via a tube or similar conduit, serves to conduct sound energy to the tympanic membrane or ear drum of a patient's ear for thus enhancing hearing capabilities.

It has been found, in practice, that the human ear canal possesses certain resonant characteristics. In free-field tests using an open canal, with 70 DB input, it has been found that from 1,000 hz to 2,800 hz there is a 12–14 DB rise, then a 10 DB drop at higher frequencies of 4,000 to 5,000 hz. Such tests have revealed that when a conventional ear mold is inserted into the ear canal, most of the resonance of the ear canal is lost. Consequently, in such instances, sound energy supplied by a hearing aid, unmodified by resonance, is conducted to the tympanic membrane. Since most hearing aids simply are incapable of greatly amplifying the higher frequencies, because of attendent feedback, the loss of resonance which attends insertion of an ear mold into the ear canal becomes a critical limiting factor in achieving maximum efficiency in the utilization of conventional hearing aids and ear mold combinations.

DESCRIPTION OF THE PRIOR ART

Conventional hearing molds generally include an ear canal component having a single chamber or longitudinal canal extended therethrough, often assuming the shape of a conical horn having a vent when in use, arranged in close proximity with a patient's tympanic membrane. Electronic amplified sound wave energy is usually air-conducted to the ear mold wherein the longitudinal canal conveys the amplified sound wave energy to the tympanic membrane, at which point normal hearing processes are commenced.

During the course of a novelty search conducted for the invention embodying the principles of the instant invention, the patents listed on the enclosed Form PTO-1449 were discovered. The body of the prior art discovered during the course of the search clearly discloses an existence of inadequacies of the aforementioned conventional ear mold. Consequently, it is believed to be readily apparent that throughout the industry it is well recognized that there exists a need for an improved ear mold having a capability of economically and practically enhancing the efficiencies of hearing aid devices.

It is therefore the general purpose of the instant invention to provide an improved acoustic ear mold for intensifying electronically-amplified sound energy utilizing an unique resonating cavity.

OBJECTS AND SUMMARY OF THE INVENTION

It is therefore an object of the instant invention to provide an improved acoustic ear mold.

It is another object to provide an improved acoustic ear mold for intensifying sound pressure for acoustic output signals derived from an electronic hearing aid.

It is another object to provide an acoustic ear mold for intensifying sound pressure for electronically-amplified sound waves prior to a delivery thereof to a patient's ear drum.

It is another object to provide an improved, practical and economic acoustic ear mold having a segmented resonating cavity defined within an elongated ear canal component adapted to be received in the ear canal of a patient, said segmented cavity being so configured and dimensioned as to collectively intensify high-frequency sounds while controlling low-frequency sounds for facilitating enhanced utility of hearing aids.

These and other objects and advantages are achieved through the use of an ear mold embodying the principles of the instant invention which preserves the resonance in the ear canal by providing an air-filled cavity which facilitates intensification of sound pressure for sound entering the ear canal from a hearing aid; with a high sound pressure produced when an input signal combines with the resonating frequency of the instant invention, sound intensification will increase and peak at 2,000, 3,000, 4,000, and 5,000 hz, the frequencies least apt to respond to conventional electronic amplification.

DESCRIPTION OF THE PREFERRED EMBODIMENT

Figure 1:
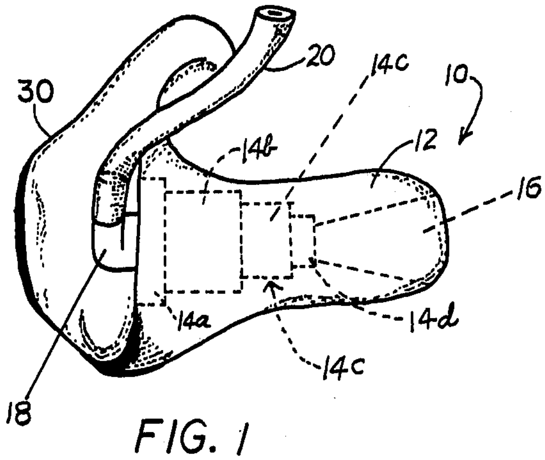
FIG. 1 is a side-elevational view of an ear mold embodying the principles of the instant invention.
Figure 3:
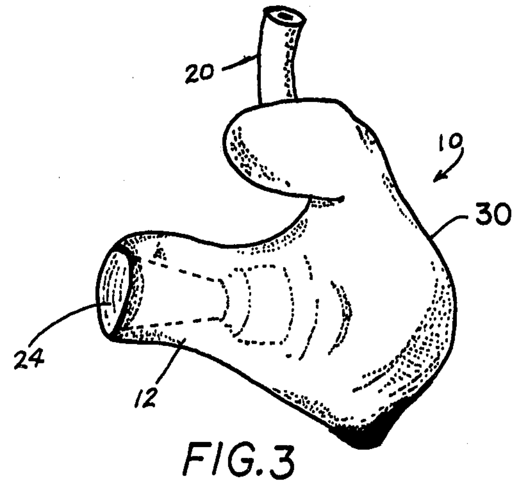
FIG. 3 is a side-elevational view of the ear mold, opposite the side shown in FIG. 1.

Referring now to the drawings, with more particularity, wherein like reference characters designate like or corresponding parts throughout the several views, there is shown in FIG. 1 an ear mold, generally designated 10, which embodies the principles of the instant invention.

The ear mold 10, as shown in FIG. 1, includes an elongated component comprising an ear canal piece, generally designated 12, suitably configured to be received within the ear canal of a patient. The component, when in place, terminates in close proximity with the patient's ear drum, not shown. The ear mold preferably is formed of a relatively rigid, synthetic resin sufficiently pliable as to be tactually compatible with the patient's ear canal.

The ear mold 10 is sometimes referred to as a "Frequency Gain Modifier Mold" due to the fact that at given frequencies, the output of the mold is characterized by a DB gain.

Figure 2:
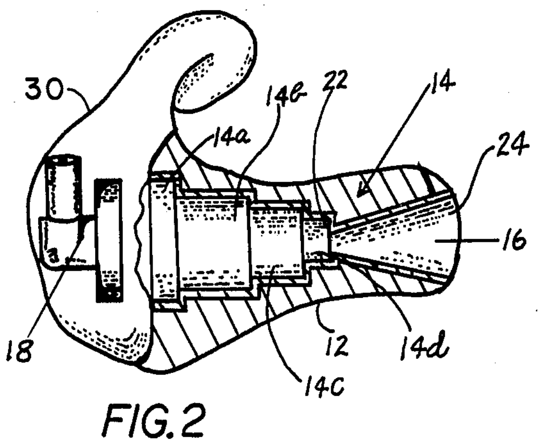
FIG. 2 is a partially exploded, cross-sectional view of the ear mold shown in FIG. 1.
Figure 5:
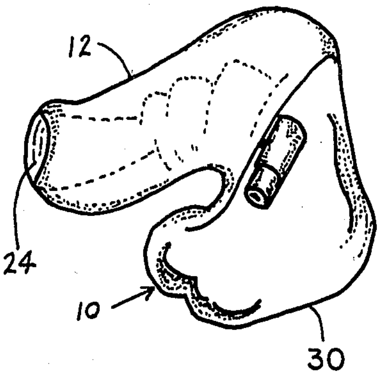
FIG. 5 is a side-elevational view, taken opposite to the view shown in FIG. 4.
Figure 4:
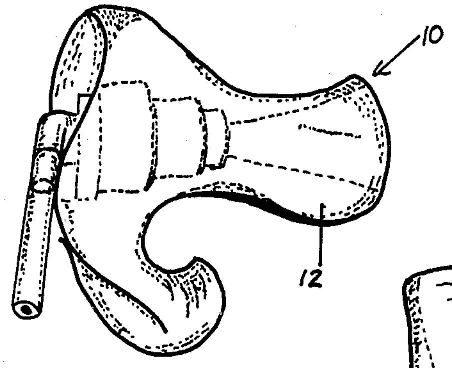
FIG. 4 is a side-elevational view taken opposite to the side shown in FIG. 1, rotated through 180° about a horizontal axis.
Figure 7:
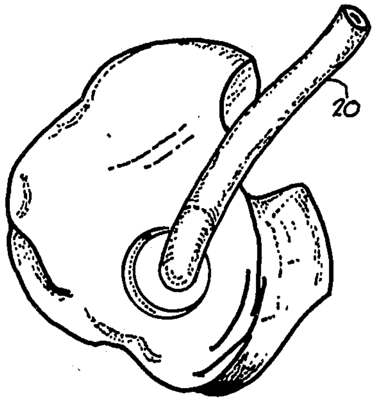
FIG. 7 is an end-elevational view of the ear mold.
Figure 6:
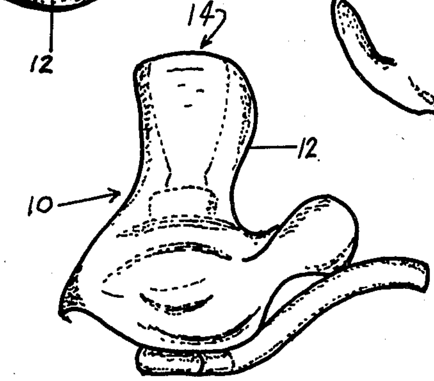
FIG. 6 is a top plan view of the ear mold.

As shown in FIG. 2, the ear piece 12 comprises a cavitated ear piece having defined therein a segmented cavity 14 coaxially aligned with an output or vent chamber 16. The cavity is formed by utilizing conventional fabricating techniques including drilling, molding and the like. The tube coupler 18 is provided for coupling the cavity 14 with a sound wave conduit 20 which serves to conduct electronically amplified sound to the cavity 14.

At the upstream end of the cavity 14, in contiguous relation with the tube coupler 18, there is a first chamber or cavity segment, designated 14a. Adjacently related to the cavity segment 14a there is a second chamber or cavity segment designated 14b. The cavity segment 14b is coaxially aligned with the first cavity segment 14a, while a third chamber or cavity segment 14c is disposed in adjacent coaxial alignment with the cavity 14b. Interposed between the cavity segment 14c and the vent chamber 16 is a fourth chamber or cavity segment, designated 14d.

It is to be understood that the cavity segments 14a–14d, as well as the vent chamber 16, are suitably shaped and dimensioned so as to enhance sound pressure intensification. Moreover, while various cavity segments may be variably dimensioned with varying degrees of success, cavity segments as follows have been found to be particularly satisfactory:

| CAVITY SEGMENT | DIAMETER OF SEGMENT | AXIAL LENGTH OF SEGMENT |
|---|---|---|
| 14a | 19/64 inches | 1/16 inches |
| 14b | ¼ inches | 5/32 inches |
| 14c | 5/32 inches | ⅛ inches |
| 14d | 0.120 inches | 1/16 inches |

It is important to appreciate that each of the cavity segments 14a–14d is of a cylindrical configuration, the length of which extends in an axial direction. The vent chamber, on the other hand, is of a truncated, frustoconical configuration having a sound-input opening, designated 22, and a sound-discharge opening or vent 24. The longitudinal dimension of the vent chamber 16 is 5/16 inches, while the smallest opening thereof is 0.20 inches and the diameter of the largest opening is 9/32.

Finally, the ear mold 10 is provided with a base end portion designated 30, of conventional design, the purposes of which is to secure the ear canal piece 10 in place within the ear canal of the wearer.

It is believed that in view of the foregoing description of the invention, the operation of the invention hereinbefore disclosed and hereinafter claimed readily is apparent. However, in the interest of completeness, the operation of the disclosed invention is, at this point, briefly reviewed.

OPERATION

In practice, the ear canal piece 12 is inserted into the ear of a patient and connected to a hearing aid, such as an electronic amplifier and transducer suitably positioned for receiving and amplifying sound waves and providing electronically amplified sound to be delivered to the air-filled cavities of the ear mold 10, via the conduit 20 and tube coupler 18. As the sound enters the segmented cavity, at cavity segment 14, the sound pressure thereof is intensified through resonance in a manner fully understood by those familiar with such devices. From segment 14a, the sound passes to the segment 14b, thence to the segments 14c and 14d to be finally delivered to the ear drum via the bent chambers 16.

The extent of the sound pressure intensification is determined, at least in part, by the particular frequency of the sound. For example, it has been found that when employing the cavity segment 14b at 2,000 hz, a fixed DB (decibel) increase in sound pressure intensification is realized. However, when employing segments 14c, 14d, and the chamber 16, along with the cavity segment 14b, a gain in intensification in the order of 10–20 decibels is realized. With the ear canal piece 12 in place and all four cavity segments 14a–14d are employed along with the vent chamber 16, a 10–60 DB gain is realized in the high-frequency range of 6,000 hz.

The effectiveness of the operation of the ear mold 10, hereinbefore described, is illustrated by the following true case history.

A patient complaining of Tinnitus Aurium in his left ear indicated that ringing was so loud, sleep at night was substantially impossible, without the aid of drugs. The patient was informed, after a complete physical examination, that he would simply have to live with the noise problem. A complete hearing evaluation was performed on the patient, by the instant inventor, using a free-acoustic field test, in which was found that the patient had a high-frequency hearing loss, and that the ringing sound was occuring in the high-frequency range of from 4,000 to 6,000 hz. The patient first was equipped with an Audiotone A-35, calibrated to P-3-MPO at 115 maximum output and a conventional ear mold with a short ear canal piece and a vent opening of 0.046 inches. The results of the test are indicated at B in FIG. 9. It is apparent that there was little help for the patient at 3,000 and 4,000 hz. The patient was then tested using an ear mold of the instant invention at the same volume as was the test conducted utilizing the conventional mold. The results of this test are indicated at C in FIG. 9. It is apparent that a large improvement over the results indicated at B occured in the 3,000 to 4,000 hz range.

After employing the hearing aid and ear mold of the instant invention for approximately one week, the patient realized enhancement in the quality of his hearing and the ringing was somewhat improved, to the point that a 5 DB increase in the volume control for the hearing aid tended to tune-out the ringing sound.

The ear mold was then adjusted slightly in order to loosen it within the canal and after using the hearing aid for another week, the patient stated that the ringing was reduced even further. After approximately one month, the patient was able to sleep at night without the use of drugs. After 10 months of using the aid, the patient indicated that he could hear and that the only time ringing occured was in the morning before the canal ear piece is inserted.

Figure 8:
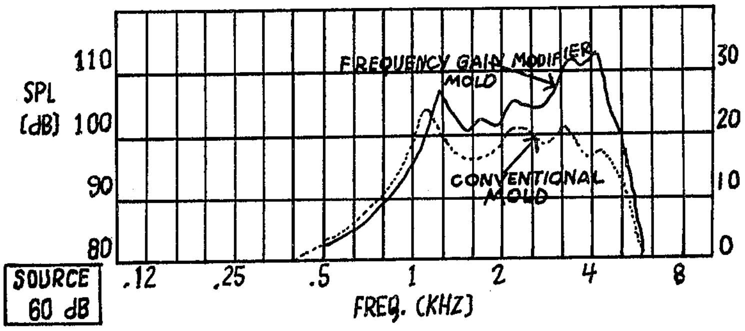
FIG. 8 is a graphic view depicting a decibel gain for the ear mold embodying the instant invention, over conventional ear molds, aforedescribed.
Figure 9:
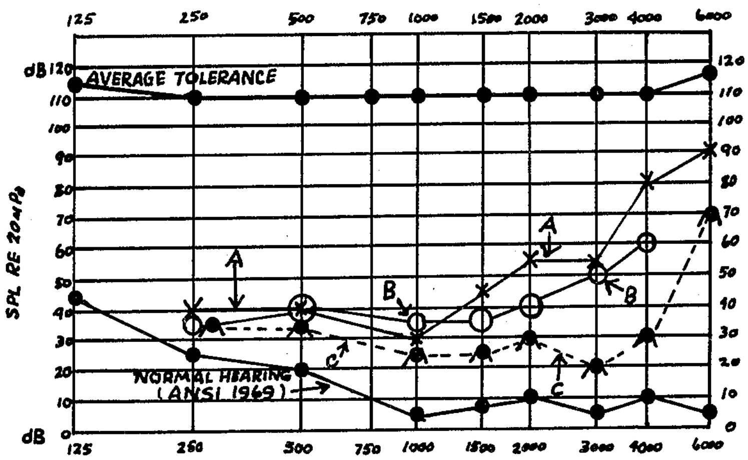
FIG. 9 is a graphic view depicting an actual case history for a patient ultimately equipped with an ear mold embodying the principles of the instant invention.

With reference to FIG. 8, it is believed important to note that the ear mold embodying the principles of the instant invention, designated FREQUENCY GAIN MODIFIER MOLD, FIG. 9, will increase the sound pressure intensity, at high frequencies in the hearing aid analyzer by 10–20 decibels over the conventional mold and 20–60 DB in the ear canal in a free-field test, depending somewhat upon the extent of cochlear damage.

It is believed that in view of the foregoing, it should now be apparent that many patients with high-frequency hearing loss now will experience an increased hearing capability and understanding, even in noisy places.

In view of the foregoing, it is believed to be apparent that the instant invention provides a practical solution to the many problems heretofore encountered by those engaged in research and development of hearing aids, ear molds, and the like.

Although the invention has been herein shown and described in what is believed to be the most practical and preferred embodiment, it is recognized that departures may be made therefrom within the scope of the invention, which is not to be limited to the illustrative details disclosed.

Having described my invention, what I claim as new and desire to secure by Letters Patent is:

1. An acoustic ear mold for amplifying sound energy, the ear mold comprising a body having a component dimensioned to be received in the ear canal of a wearer, said component having a vent chamber therein communicating with the exterior of the component through a sound-discharge opening and a resonating cavity communicating with the vent chamber at one end and the exterior of the body at an opposite end remote from said vent chamber so as to form a passage composed of the resonating cavity and vent chamber extending through the body and said resonating cavity having a plurality of chambers aligned in series relation and being of progressively smaller transverse dimension in the direction of said vent chamber for amplifying sound energy received in said resonating cavity.

2. The acoustic ear mold of claim 1 wherein said passage extends only along a single longitudinal axis so as to communicate with the exterior of the passage only through said opposite end and through the sound-discharge opening thereby to amplify sound energy received at said opposite end during transmission along said passage for release from the sound-discharge opening.

3. The acoustic ear mold of claim 2 wherein the chambers of the resonating cavity are each of a substantially cylindrical configuration varying in diameter from each other such that the chamber of largest diameter is nearest said opposite end of the passage and the chamber of smallest diameter communicates directly with the vent chamber.

4. The acoustic ear mold of claim 3 wherein the vent chamber is of a truncated substantially conical configuration enlarging in a direction away from the resonating cavity and toward the sound-discharge opening.

5. The acoustic ear mold of claim 3 wherein each chamber of the resonating cavity joins the adjacent next diametrically smaller chamber at a shoulder surface substantially right-angularly related to said longitudinal axis of the passage.

6. An acoustic ear mold for intensifying sound pressure for an acoustic output from an electrical hearing aid worn by a wearer, comprising:

A. a body formed of synthetic resin and having:
   1. an ear canal component suitably configured to be received within the ear canal of said patient,
   2. a segmented, air-filled, resonating cavity defined in said component including four coaxially aligned, contiguous cavity segments arranged in communicating relation for intensifying sound pressure in the range of 250 Hz to 6,000 Hz, said segments having diameters different from each other with the axial length of the opposite end-most segments being substantially identical and the axial length of the inner segments being different from each other and different from that of said end-most segments, and
   3. a substantially truncated conical cavity defined in said component, an acoustic output chamber extended from said cavity to the terminous of the component for delivering from said cavity to the ear drum of said wearer, pressure-intensified acoustic signals, said output chamber being characterized by a vent opening located at the terminous of the component, and an input opening located adjacent one of said end-most cavity segments, said vent opening being characterized by a diameter greater than that of said input opening; and B. a tubular conduit coupled with the hearing aid and with said cavity for conveying acoustic signals from the output of the hearing aid to said cavity to be intensified through frequency gain modification.

* * * * *